(12) United States Patent
Sass

(10) Patent No.: US 6,383,215 B1
(45) Date of Patent: May 7, 2002

(54) METHOD AND INTRAVASCULAR STENT FOR REDUCING COMPLICATIONS AFTER IMPLANTATION OF AN INTRAVASCULAR STENT

(76) Inventor: Norbert Sass, Kutschwerstieg 15, 21684 Stade (DE)

( * ) Notice: Subject to any disclaimer, the term of this patent is extended or adjusted under 35 U.S.C. 154(b) by 0 days.

(21) Appl. No.: 09/839,249

(22) Filed: Apr. 20, 2001

(30) Foreign Application Priority Data

Feb. 13, 2001 (DE) .......................... 101 07 795

(51) Int. Cl.$^7$ .................................................. A61F 2/06
(52) U.S. Cl. ..................................... 623/1.15; 623/1.46
(58) Field of Search ............................... 623/1.11–1.23, 623/1.46, 1.47, 1.48, 1.49, 1.5–54, 901

(56) References Cited

U.S. PATENT DOCUMENTS 5,866,561 A * 2/1999 Ungs ........................ 514/182
6,197,013 B1 * 3/2001 Reed et al. ................. 604/509

* cited by examiner

Primary Examiner—Henry J. Recla
Assistant Examiner—(Jackie) Tan-Uyen T. Ho
(74) Attorney, Agent, or Firm—Mallinckrodt & Mallinckrodt; Robert R. Mallinckrodt

(57) ABSTRACT

An intravascular stent reduces the risk of restenosis due to stent implantation by using 17beta-estradiol as a vessel healing substance after implantation of an intravascular stent. The 17beta-estradiol coats at least a portion of the surface of the stent and is adhered to the stent with an adhesive layer containing DLC ("diamond-like carbon"). 17beta-estradiol inhibits the growth of smooth muscle cells and stimulates the re-endothelialization after implantation of an intravascular stent.

4 Claims, 3 Drawing Sheets

METHOD AND INTRAVASCULAR STENT FOR REDUCING COMPLICATIONS AFTER IMPLANTATION OF AN INTRAVASCULAR STENT

BACKGROUND OF THE INVENTION

This invention relates to a method for reducing complications after implantation of an intravascular stent and, more particularly, for reducing the risk of restenosis due to stent implantation.

The invention further relates to a method for producing an intravascular stent reducing complications after implantation into a vessel and, more particularly, reducing the risk of restenosis due to stent implantation.

The invention further relates to the use of vessel healing substances after implantation of an intravascular stent and, more particularly, to the use of vessel healing substances during manufacture of an intravascular stent.

The invention finally relates to an arrangement for coating one or more intravascular stents with a coating substance.

An intravascular stent is a prosthesis which may be placed within a body passageway containing endothelial cells such as any vein, artery or blood vessel within the vascular system. Typically, the stent is inserted into a vessel and placed at a site of vascular occlusion. The stent is expanded at this site in order to contact the vessel wall, thereby widening the vessel and providing mechanical support for the wall. Stents are typically manufactured from special tubes of metal or other material compositions (e.g. stainless steel, tantalum, nitinol) or from coil or plait structures of metal and/or plastics. The stents may be inserted into the vessel in different ways. Before it is inserted, the stent can e.g. be arranged on a support and crimped thereupon. The support can be a balloon catheter. The crimped stent is then transported by means of the balloon catheter into the vessel to the site of stent placement. The stent is fixed in the vessel by being expanded, e.g. by increasing the internal pressure of the balloon catheter by means of a pump, e.g. a hand pump. Thereby, the structure of the stent is deformed and the stent urges against the wall of the vessel. After the balloon catheter has been removed, the stent is dimensionally stable in the vessel. A similar process is used for inserting so called self-expandable stents. These stents do not need any external pressure in order to expand, they expand due to restoring forces or due to the ambiance conditions (flow, temperature etc.). Thus, an inserted stent expands and support the vessel wall and can eliminate stenosis.

However, it has been found that the presence of a stent in a vessel can result in complications, e.g. restenosis. Restenosis can e.g. take place at the ends of the sent or in the stent itself ("in-stent stenosis"). It is believed that restenosis take place as a natural healing reaction due to the expansion of the vessel and the mechanical action of the stent on the wall of the vessel. Due to the uncontrolled migration and proliferation of medial smooth muscle cells the vessel is again stenosed. Also, the stent can cause undesirable local thrombosis.

Stents have been used for medical treatment since 1990. Since then, the experts deals in a large numbers of examinations and essays with the problem of complications after insertion of stents (see e.g. "Local drug delivery for prevention of restenosis" by A. Michael Lincoff et al. in Circulation 90(4), October 1994 and "New recipes for in-stent restenosis: cut, grate, roast or sandwich the neointima?" by C. Di Mario et al. in Heart 84(5), 2000).

Several different method for preventing complications due to stent implantation have been proposed. To address the problem of thrombosis the person receives anticoagulant and antiplatelet drugs (e.g. ticlopidin or aspirin). To address the problem of restenosis and in-stent stenosis the vessel can be expanded again by means of a balloon catheter. Often even bypass surgery is required. Furthermore, the stents can be coated with different substances such as heparin, collagen, fibrin or adhesion peptide coating in order to reduce the risk of restenosis. It is also known to coat the stent with DLC ("diamond-like carbon") in order to reduce the risk of restenosis.

Such methods and stents are e.g. disclosed in U.S. Pat. Nos. 6,153,252, 6,140,127 and 5,591,227.

Prior attempts to reduce complications after implantation of an intravascular stent could not reduce the risk of restenosis in a satisfactory way. Restenosis and in-stent stenosis are still considered as unsolved problems. For example, in-stent stenosis is still observed in 20%–30% of the cases.

SUMMARY OF THE INVENTION

The object of the present invention is hence to reduce complications after implantation of an intravascular stent and, more particularly, to reduce the risk of restenosis due to stent implantation.

A more specific objects of the present invention is to provide an effective method for reducing complications after implantation of an intravascular stent and, more particularly, to reduce the risk of restenosis due to stent implantation.

Another object of the invention is to provide a method for producing an intravascular stent effectively reducing complications after implantation into a vessel and, more particularly, reducing the risk of restenosis due to stent implantation.

Still another object of the invention is to provide an effective method for coating one or more intravascular stents with a coating substance.

In accordance with the invention these objects are achieved by using 17beta-estradiol as vessel healing substance after implantation of an intravascular stent.

The invention is based on the knowledge that some of the complications after implantation of an intravascular stent (e.g. the risk of restenosis or in-stent stenosis) is caused by the excessive smooth muscle cell growth in the vessel wall. This excessive growth take place when the endothelium is injured. It has been shown that it takes about two month after implantation of a stent in a human body before it is covered by neointima and endothelial cell such that a continuous cell layer is developed.

The invention is further based on the knowledge that 17beta-estradiol (chemically described as 1,3,5(10)-estradien-3,17beta-diol having the chemical notation $C_{18}H_{24}O_2$) on one hand inhibits the growth of smooth muscle cells and, on the other hand, stimulates the re-endothelialization. The present invention makes use of these effects in order to prevent restenosis and in-stent stenosis.

17beta-estradiol is a natural estrogen produced in the body itself. Thus, there are no problems concerning the biocompatibility when using 17beta-estradiol.

Thus, in accordance with one aspect of the invention the above mentioned objects are achieved through a method for reducing complications after implantation of an intravascular stent, comprising the steps of inserting an intravascular stent into a vessel to a site of intravascular stent placement and supplying 17beta-estradiol to the site of intravascular stent placement.

The supply of 17beta-estradiol can be effected before, during or after the implantation of the stent. However, it can be advantageous to supply 17beta-estradiol at least during the operation for implantation of the stent into the vessel or even simultaneously with the implantation of the stent into the vessel. This ensures that no additional surgical operation has to be done in order to supply the 17beta-estradiol. Furthermore, this increases the probability that the 17beta-estradiol is supplied to the proper place, namely the site of stent placement.

The quantity of 17beta-estradiol supplied to the site of stent placement can be chosen in dependence of the estimated healing time of the vessel after implantation of the stent. Preferably, the quantity of 17beta-estradiol is chosen such that the time of action of the 17beta-estradiol is substantially equal to the estimated healing time. Depending on the individual case, a quantity of 10–1000 μg 17beta-estradiol can be suitable. This quantity will, among other things, depend on the use of the 17beta-estradiol as one single dose acting within a few hours or as continuous (or discontinuous) supply over a longer period of time.

The supply of 17beta-estradiol during the implantation of the stent can be effected by using different known supply methods as used for supplying other drugs into the human body. A particular advantageous method is given by a further aspect of the present invention, according to which the supply of 17beta-estradiol is effected by means of a drug elution system applied to the intravascular stent. This ensures that the supply of 17beta-estradiol can be effected simultaneous with the implantation of the stent into the vessel and that the 17beta-estradiol is supplied to the proper place, namely the site of stent placement.

In accordance with a further aspect of the invention the above mentioned objects are achieved through a method for producing an intravascular stent reducing complications after implantation into a vessel, comprising the steps of providing a stent body suitable for implantation and applying 17beta-estradiol to the stent body. It is important that the 17beta-estradiol is connected to the stent in such a way, that it can act in a suitable manner after implantation of the stent. This can be achieved in that the 17 beta-estradiol is provided on the surface of the stent body.

Known intravascular stents have a stent body defining an inner and an outer surface. Such stents are known e.g. as ring-coil stents, wire stents and tubular stents. The 17beta-estradiol can be provided on the inner surface and/or on the outer surface of this stent body. However, it is advantageous to provide 17beta-estradiol on the inner surface as well as on the outer surface of the stent body.

In some cases, the material of the stent body has not suitable adhesive properties for the 17beta-estradiol. In these cases, measures can be taken in order to improve the adhesive property. This can be achieved in that the surface of the stent body is provided with an adhesive layer for the 17beta-estradiol e.g. on the inner surface and/or on the outer surface. It has been found that DLC ("diamond-like carbon") is suitable for this purpose.

If it is desired to let the 17 beta-estradiol act a longer period of time, it is advantageous to apply the 17beta-estradiol to the stent together with a drug elution system. In such drug elution systems the drug (here: 17beta-estradiol) is bonded in other substances and the supply of the drug at the site of placement can be effected by elution in a defined manner as a function of time. Such drug elution system are well known for other drugs and described e.g. in U.S. Pat. No. 6,153,252 which is hereby incorporated by reference. These known drug elution systems can be used in a corresponding manner for eluting 17beta-estradiol.

In accordance with a further aspect of the invention the 17beta-estradiol is applied to the surface of a stent body by means of a surface coating process. this can be effected directly on the surface of the stent body or on a support or adhesive layer. A large number of different surface coating processes are known which can be used for this purpose. It has been shown that CVD processes ("chemical vapor deposition processes") are particularly suitably. During such processes the coating substance is vaporized and is then deposited to the bodies to be coated. For this purpose the stent body to be coated with 17beta-estradiol can be inserted together with 17beta-estradiol into a vacuum chamber. The 17beta-estradiol is then vaporized e.g. by heating. It has been found that it is advantageous to heat the chamber wall of the vacuum chamber (or at part of it) during this coating process thereby reducing the deposition of 17beta-estradiol on the chamber wall. The effectiveness of the coating process can be further increased by cooling the stents to be coated. If a plurality of stents is to be coated with 17beta-estradiol at the same time in the vacuum chamber, these stents can be cooled by means of common cooling means, e.g. a cooling water circulation system.

In many applications it will be desirable to determined the quantity of 17beta-estradiol applied to the stent. Using a coating process this can be achieved by coating the stent with a layer of 17beta-estradiol having a predetermined thickness. This can be achieved by determining layer thickness parameters during coating. One such parameter can be defined by measuring the thickness of the layer using known methods of measuring layer thickness. However, there are also other parameters suitable for this determination, e.g. the duration of the coating process. Then the layer thickness is determined (e.g. experimentally) as a function of the duration of the coating process. Of course, further parameters (e.g. temperature of the 17beta-estradiol, of the stents and of the walls of the vacuum chamber) having an influence on this function have to be taken into consideration. These further parameters can be kept constant such that the layer thickness will depend only on the duration of the coating process. By this method the layer thickness can be determined and controlled very exactly.

Thus, in one aspect of the invention the coating process of one or several stents can be achieved in an arrangement comprising a vacuum chamber having a chamber wall, stent accommodation means for accommodating the stent or the stents in the vacuum chamber, substance accommodation means for accommodating the coating substance in the vacuum chamber, and vaporization means for vaporizing the coating substance in the vacuum chamber to achieve a coating process through which the stents are coated with the coating substance. Such an arrangement can, of course, be used for coating stents with coating substances other than 17beta-estradiol.

However, it shall be noted, that the 17beta-estradiol (if desired together with further substances) can be applied to the stents by other methods, e.g. by spraying or by dipping the stents into a solution. Such methods are well known for other substances and described e.g. in U.S. Pat. No. 6,153, 252 incorporated herein by reference. It can be advantageously to carry out these methods in a vacuum chamber.

All stents or stent bodies known in the prior art can be provided with 17beta-estradiol according to the present invention, provided that the 17beta-estradiol can adhere to the surface of the stent in same way. Several of such known stents are mentioned in U.S. Pat. No. 6,153,252 and hereby incorporated by reference.

Further objects and features of the invention will be apparent to a person skilled in the art from the following specification of preferred embodiments when read in conjunction with the appended claims.

BRIEF DESCRIPTION OF THE DRAWING

The invention and its mode of operation will be more clearly understood from the following detailed description when read with the appended drawing in which.

DESCRIPTION OF THE PREFERRED EMBODIMENTS

Figure 1:
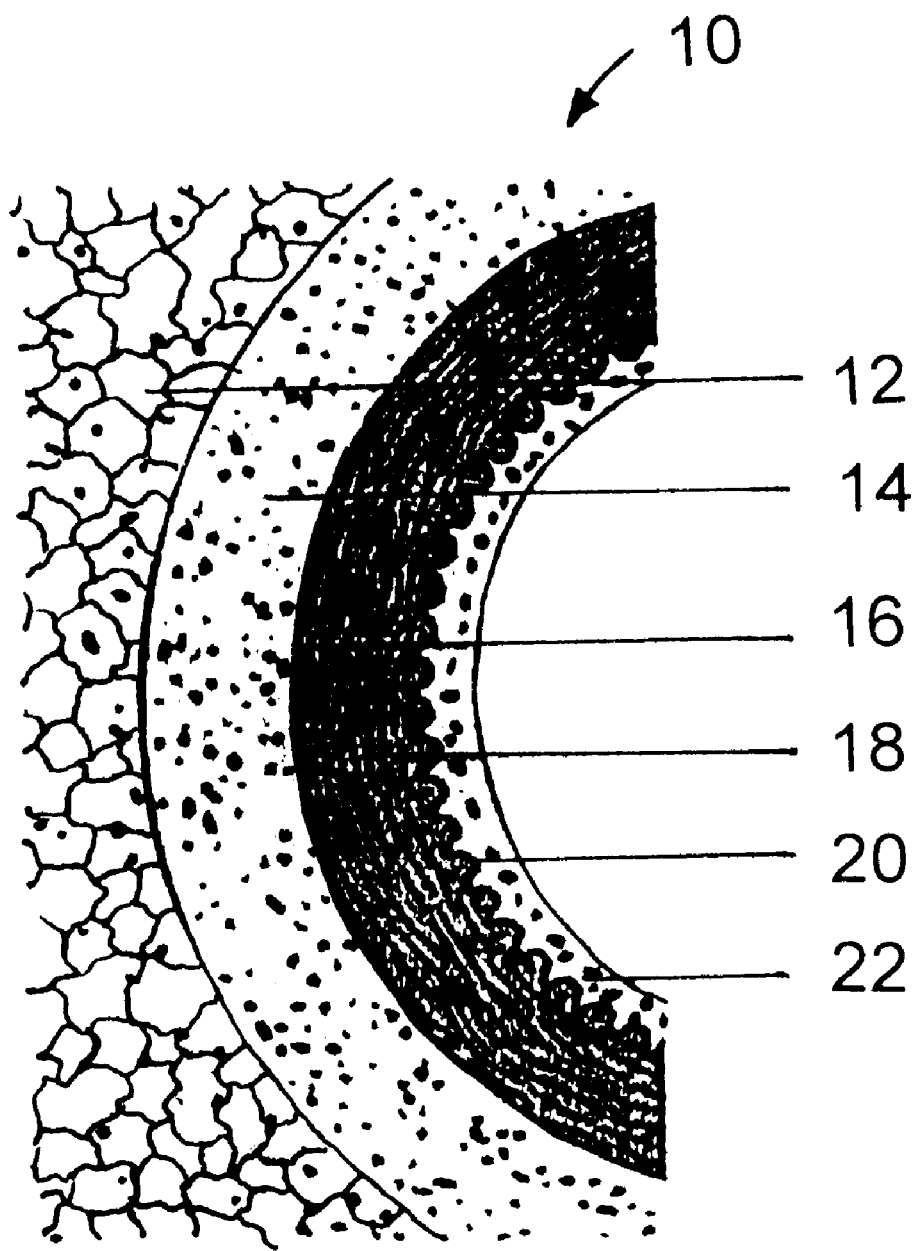
FIG. 1 is a schematic illustration and shows a cross section of a blood vessel.

Referring now to FIG. 1, for better understanding there is shown a section of a cross section of a blood vessel 10. In this case it is the wall construction of a muscular artery vessel. Numeral 12 designates the fat tissue in which the blood vessel is embedded. The outer layer ("tunica externa") of the blood vessel 10 is designated by numeral 14. An outer membrane 16 ("membrana elastica externa") separates the outer layer 14 from a mid-layer 18 ("tunica media"). An inner membrane 20 ("membrana elastica interna") separates the mid-layer 18 from an inner layer 22 ("tunica intima"). The inner layer consists of endothelium. The endothelium is a very thin layer having a monolayer of endothelial cells. The mid-layer 18 contains smooth muscle cells.

If the inner layer 22 of the blood vessel 10 is injured, then the mid-layer 18 is exposed to the blood flowing in the blood vessel 10, the smooth muscle cells in the mid-layer 22 getting into contact with the blood. Blood comprises several substances which stimulates the growth of smooth muscle cells. This can lead to narrowing or occlusion of the blood vessel if this growth is not suppressed. This growth of smooth muscle cells can be effectively suppressed by inhibiting this growth and by fast re-endothelialization, that means healing of the inner layer 22.

Figure 2:
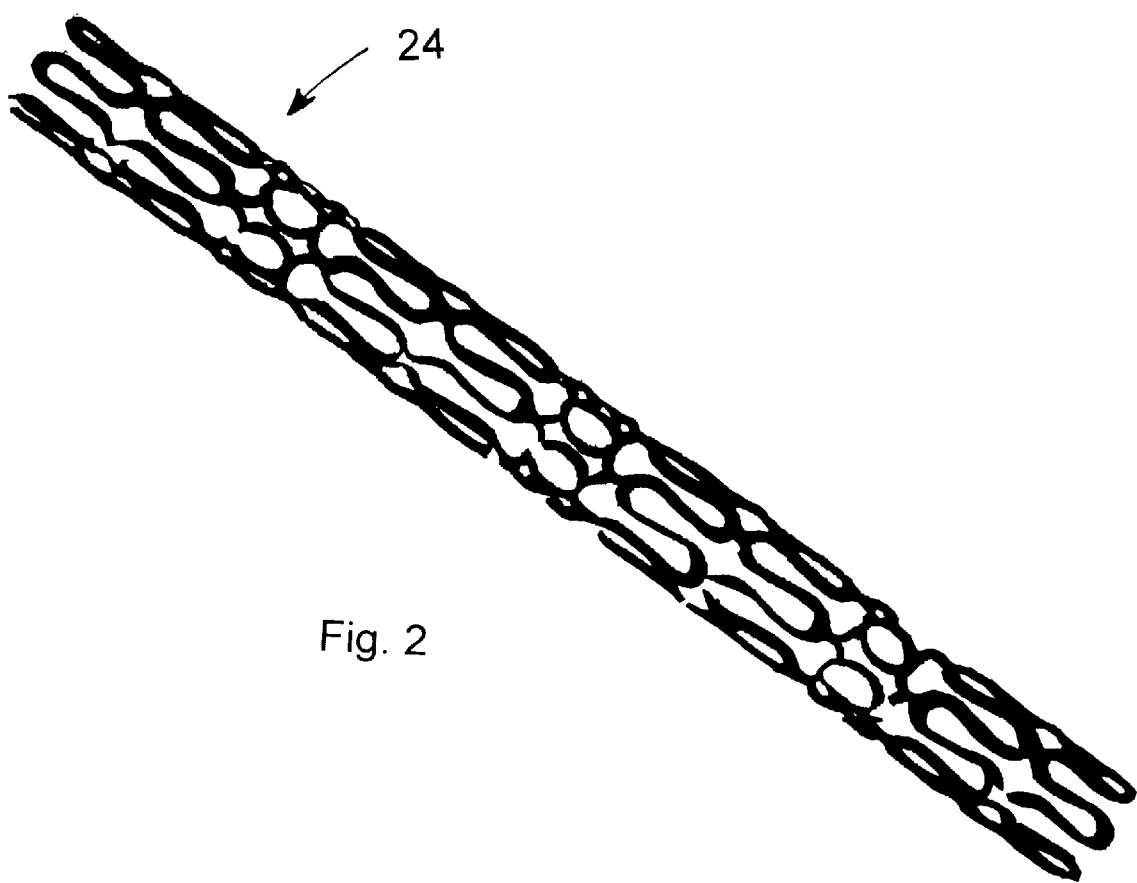
FIG. 2 is a perspective illustration and shows a stent coated with DLC and 17beta-estradiol.
Figure 3:
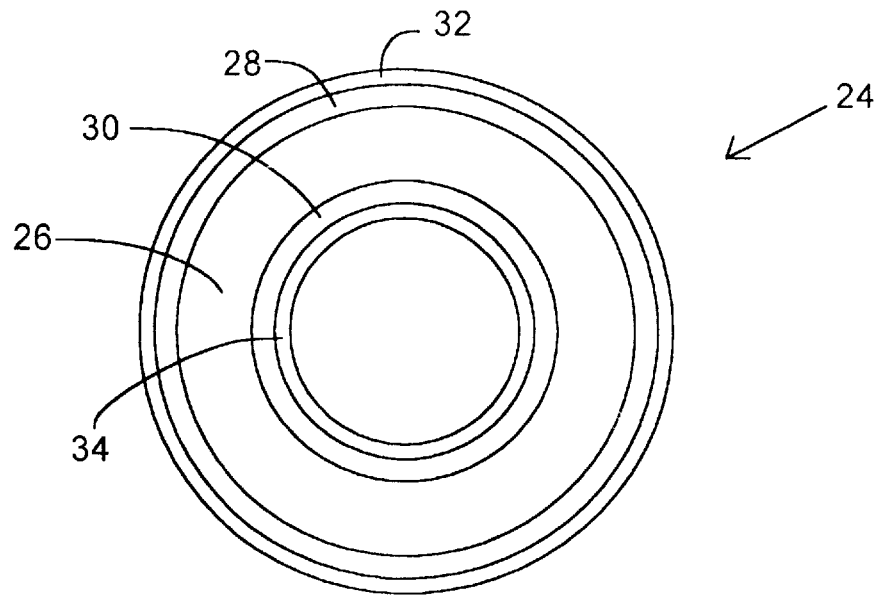
FIG. 3 is a schematic illustration and shows a cross section of the stent of FIG. 2.

With reference to FIG. 2, there is shown a stent 24. This stent has a stent body 26 consisting of a mesh of stainless steel ("316L"). This is a commercially available stent intended to be crimped in a crimping device before implantation. The surface of the stent body 26 is coated with DLC. This is illustrated in FIG. 3 by an outer and an inner DLC-layer 28 and 30, respectively. The surface of the DLC-layers 28 and 30 are coated with 17beta-estradiol. This is illustrated in FIG. 3 by an outer and an inner 17beta-estradiol-layer 32 and 34, respectively.

Figure 4:
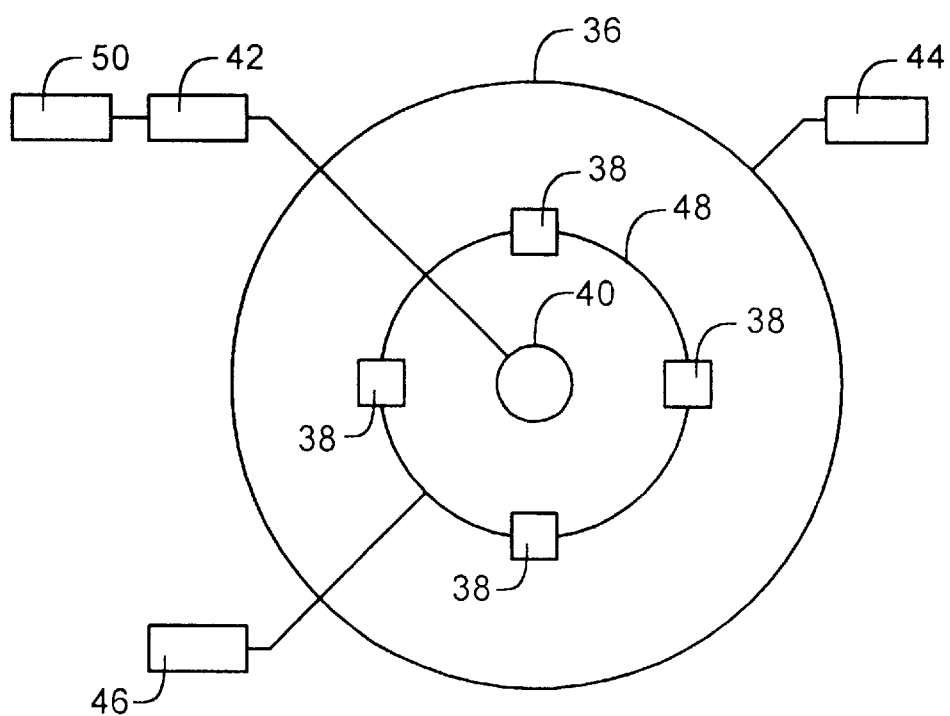
FIG. 4 is a schematic illustration and shows a plan view of an arrangement for coating stents by means of a CVD process.

With reference to FIG. 4, there is shown an arrangement for coating stents by means of a CVD process. The arrangement comprises a vacuum chamber 36. Stent accommodation means in the form of stent supports 38 are provided in the vacuum chamber 36. (In the schematic illustration of FIG. 4 there are shown, as example, four such stent supports 38.) Furthermore, substance accommodation means in the form of an accommodation vessel 40 for accommodating for accommodating a coating substance (here: 17beta-estradiol) is provided in the vacuum chamber 36. The accommodation vessel 40 is adapted to be heated by a heating device illustrated by block 42. The wall of the vacuum chamber 36 is adapted to be heated by a further heating device illustrated by block 44. The stent supports 28 are adapted to be cooled by a cooling device illustrated by block 46. The stent supports 38 are connected to a common cooling water circulation system 48.

The heating device 42 for heating the accommodation vessel 40 is connected to a timer 50, by means of which the heating time of the heating device 42 is controlled.

In order to manufacture a stent according to the method described herein, at first the stent body 26 is produced out of stainless steel. Subsequently, the stent body 26 is coated with DLC-layers 28 and 30. This is known in the prior art and therefore not described in detail herein. The stent body 26 coated with DLC is inserted into one of the stent supports 38 (possibly together with further stent bodies in further stent supports 38). 17beta-estradiol is inserted into the accommodation vessel 40 in a form which is suitable for vaporization.

For this purpose, the 17beta-estradiol can be dissolved in a suitable organic solvent. Subsequently, the vacuum chamber 36 is closed and a vacuum is generated in the chamber 36.

The stent supports 38 and, thus, the stents supported therein, are cooled to a defined temperature by means of the cooling device 46 and the cooling water circulation system 48. The walls of the vacuum chamber 36 are heated to a defined temperature by means of the heating device 44. By means of the heating device 42 the accommodation vessel 40 and, thus, the 17beta-estradiol-solution therein, is heated to a defined temperature or by following a defined march of temperature, the timer 50 being set to switch off the heating device 42 after e predetermined time period.

The temperatures defined by the heating devices 42 and 44 and by the cooling device 46 and the time period defined by the timer 50 are predetermined in such a manner, that the stents supported in the stent supports 38 are coated with 17beta-estradiol in a desired manner and with a desired layer thickness. These parameters can be selected such that the stent is coated with, for example, 30–50 µg 17beta-estradiol.

When a stent coated with 17beta-estradiol is inserted into a blood vessel, it is ensured that the 17beta-estradiol is supplied to the site of stent placement. The supply of 17betaestradiol is then effected simultaneous with the implantation of the stent. By proper setting the parameters it can be ensured that the quantity of 17beta-estradiol is chosen to substantially correspond to the healing time of the vessel after implantation of the stent.

I claim:

1. An intravascular stent having an inner surface and an outer surface;
   an adhesive layer containing DLC ("diamond-like carbon") on said inner surface and/or said outer surface of the stent body; and
   17beta-estradiol on said adhesive layer on said inner surface and/or said outer surface of the stent body.

2. A method for producing an intravascular stent reducing complications after implantation into a vessel comprising the steps of:
   providing a stent body suitable for implantation, said stent body having an inner surface and an outer surface;
   providing an adhesive layer containing DLC ("diamond-like carbon") on said inner surface and/or said outer surface of the stent body; and applying 17beta-estradiol to said adhesive layer on said inner surface and/or said outer surface of the stent body.

3. An intravascular stent having a surface containing 17beta-estradiol on an adhesive layer containing DLC ("diamond-like carbon") on at least a portion of the surface.

4. A method for producing an intravascular stent reducing complications after implantation into a vessel, comprising the steps of:

providing a stent body suitable for implantation, said stent body having a surface;

providing an adhesive layer containing DLC ("diamond-like carbon") on at least a portion of the stent body surface; and applying 17beta-estradiol to said adhesive layer.

* * * * *